United States Patent [19]
Baur et al.

[11] Patent Number: 5,968,546
[45] Date of Patent: Oct. 19, 1999

[54] KERATINOCYTE CULTURE FROM PRECURSOR CELLS

[76] Inventors: Marcus Baur, Le-Grand-Chemin 5400, CH-1066 Epalinges; Thomas Hunziker, Schulthesserstrasse 20, CH-3653 Oberhofen; Alain Limat, Juchstrasse 3, CH-1712 Tafers, all of Switzerland; Wolfram Riedel, Johann-Keller-Weg 6a, D-869198 Utting; Christian Toloczyki, Seefelder Hofberg 11b, D-86919 Utting, both of Germany

[21] Appl. No.: 09/079,160

[22] Filed: May 15, 1998

Related U.S. Application Data

[60] Provisional application No. 60/046,906, May 16, 1997.

[51] Int. Cl.$^6$ .............................. A61L 15/16; C12N 5/02; A61K 47/30
[52] U.S. Cl. ...................... 424/444; 435/384; 514/772.3; 514/774
[58] Field of Search ............................ 424/444; 435/384; 514/772.3, 774

[56] References Cited

U.S. PATENT DOCUMENTS 5,580,781  12/1996  Naughton et al. ....................... 435/1.1

*Primary Examiner*—Carlos A. Azpuru
*Attorney, Agent, or Firm*—Ivor R. Eirifi; Mintz, Levin, Cohn, Ferris, Glovsky and Popeo, P.C.

[57] ABSTRACT

The present invention relates to the treatment of skin defect by organotypically cultured autologous keratinocytes isolated from the outer root sheath of hair follicles. Methods for primary as well as subsequent organotypic cultures (epidermal equivalents) in fully defined media eventually supplemented by autologous human serum and substances isolated from blood components, with minimal allogeneic biological supplements, are disclosed. Techniques to prepare epidermal equivalents for transplantation are included, as well as a method for the transport of the epidermal equivalents.

19 Claims, No Drawings

KERATINOCYTE CULTURE FROM PRECURSOR CELLS

This application claims priority on provisional application Ser. No. 60/046,906 filed on May 16, 1997, the entire contents of which are hereby incorporated by reference.

BACKGROUND OF THE INVENTION

Healing of skin defects progresses through three general phases, i.e., (1) inflammation, (2) wound cell migration and mitosis, and (3) extracellular matrix production and remodelling. The ordered sequence of these events is thought to be orchestrated by interactions among cells, growth factors, and extracellular matrix proteins. A crucial step of skin wound healing is epidermal regeneration, i.e., re-epithelialization. Besides interfollicular epidermal keratinocytes from the wound edges, the outer root sheat (ORS) cells from residual hair follicles also contribute to this process (Eisen et al., J Invest Dermatol 15: 145–156, 1955). The ORS of hair follicles is comprised largely of undifferentiated keratinocytes that encompass the cylindrical structures of the hardened inner root sheath and the hair shaft (Montagna and Parakkal, pp. 172–258 in "The Structure and Function of Skin", c. 1974 by Academic Press New York, N.Y.). Recent literature indicates that ORS cells are at a lower level of commitment to differentiation than the basal interfollicular keratinocytes (Coulombe et al., J Cell Biol 109: 2295–2312, 1989; Limat et al., Exp Cell Res 194: 218–227, 1991; Limat et al., Cell Tissue Res 275: 169–176, 1994), and label retaining cells have been detected in the animal as well as the human ORS region near the bulge area which possibly represent stem cells for skin epithelial tissues (Cotsarelis et al., Cell 61: 1329–1337, 1990 Kobayashi et al., Proc Natl Acad Sci USA 90: 7391–7395, 1993; Yang et al., J Invest Dermatol 105: 14–21, 1993; Rochat et al., Cell 76: 1073–1076, 1994; Moll, J Invest Dermatol 105: 14–21, 1995). Human ORS cells isolated from plucked anagen scalp hair follicles can be expanded extensively in vitro (Weterings et al., Brit J Dermatol 104: 1–5, 1981; Limat and Noser, J Invest Dermatol 87: 485–488, 1986; Imcke et al., J Am Acad Dermatol 17: 779–786, 1987; Limat et al., J Invest Dermatol 92: 758–762, 1989). Under conventional submerged culture conditions, ORS cells resemble interfollicular epidermal keratinocytes by both morphologic and biochemical (e.g., keratin profiles) criteria (Stark et al., Differentiation 35: 236–248, 1987; Limat et al., J Invest Dermatol 92: 758–762, 1989; Limat et al., Ann NY Acad Sci 642: 125–147, 1991). In organotypic cocultures with human dermal fibroblasts, i.e., under conditions mimicking the epidermal environment, ORS cells with respect to histological, immunohistological, ultrastructural and biochemical criteria develop a stratified epithelium reminiscent of regenerating epidermis (Lenoir et al., Dev Biol 130: 610–620, 1988; Limat et al., Exp Cell Res 194: 218–227, 1991; Limat et al., Ann NY Acad Sci 642: 125–147, 1991). If such organotypic cultures are grafted onto nude mice, ORS cells form a regular neo-epidermis that is under homeostatic control (Limat et al., Transplantation 59: 1032–1038, 1995). Thus, human ORS cells are of considerable interest for clinical application.

In the last decade, interest has focused on the use of cultured epithelial cells for wound coverage. First, sheets of cultured autologous interfollicular keratinocytes were grafted successfully on acute wounds, mainly in the treatment of larger third degree burns (O'Connor et al., Lancet 1: 75–78, 1981; Compton et al., Lab Invest 60: 600–612, 1989) but also of epidermolysis bullosa (Carter et al., J Am Acad Dermatol 17: 246–250, 1987), pyoderma gangrenosum (Dean et al., Ann Plast Surg 26: 194–195, 1991; Limova and Mauro, J Dermatol Surg Oncol 20: 833–836, 1994), and wounds after excision of giant congenital nevi (Gallico et al., J Plast Reconstr Surg 84: 1–9, 1989) or separation of conjoined twins (Higgins et al, J R Soc Med: 108–109, 1994).

In contrast to the treatment of acute wounds, grafting of chronic wounds such as leg ulcers with cultured keratinocytes has been much less successful. Allografts do not result in a permanent take (Fabre, Immunol Lett 29: 161–166, 1991) and thus may be classified as a quite effective but expensive biological dressing (reviewed by Phillips et al., J Am Acad Dermatol 21: 191–199, 1989). A reproducible, major definite take of autologous keratinocyte grafted by various modalities—sheets of submerged keratinocyte cultures consisting of only a few, noncornified cell layers (Hefton et al., J Am Acad Dermatol 14: 399–405, 1986; Leigh and Purkis, Clin Exp Dermatol 11: 650–652, 1986; Leigh et al., Brit J Dermatol 117: 591–597, 1987; Philips et al., J Am Acad Dermatol 23: 189–198, 1990; Giannotti et al., G Ital Dermatol Venerol 125: 161–167, 1990; Harris et al., Clin Exp Dermatol 18: 417–420, 1993), trypsinized single cells attached to collagen-coated dressings (Brysk et al., J Am Acad Dermatol 25: 238–244, 1991), skin equivalents (Mol et al., J Am Acad Dermatol 24: 77–82, 1991)—has not been convincingly documented. The same holds true for reports on grafting of freshly isolated, autologous interfollicular keratinocytes (Hunyadi et al., J Dermatol Surg Oncol 14: 75–78, 1988) or ORS cells (Moll et al, Hautarzt 46: 548–552, 1995) fixed to the wound bed by a fibrin glue. Disadvantages of bovine serum used during cultivation of the keratinocytes may contribute to reduced take rate, since it resists in keratinocytes (Johnson et al., J Burn Care Rehab 11: 504–509, 1990).

SUMMARY OF THE INVENTION

It is an object of the present invention to generate keratinocytes from outer root sheath cells (ORS cells) in fully defined culture conditions for the treatment of skin defects, especially chronic wounds such as leg ulcers, diabetic ulcers, pressure sores in human and animal organisms. Besides the treatment of wounds, the keratinocytes may be used in plastic and cosmetic surgery, whenever there is a demand for skin support, e.g., post operative after removal of tattoos, naevi, skin cancer, papillomas, after amputation, in sex transformation or re-virginisation.

It is a further object of the present invention to generate highly differentiated organotypic cultures of ORS cells, so-called dermal equivalents or epidermal equivalents, to treat skin defects, especially chronic wounds.

It is a further object of the invention to produce dermal or epidermal equivalents using only a minimum of allogenic or heterogenic biological supplements in the culture process.

An object of the invention is also to minimize the risk of disease transmission, e.g., by clinical use of blood products, by using autologous serum and substances released from blood components, e.g., blood platelets, from the patients to be treated, for supplements in in vitro culturing steps.

A further object of the invention is a transport system to enable transportation of the dermal and/or epidermal equivalents from the generating facility to the institution treating the patients. Such a transport system is preferably robust to conditions encountered in delivery by mail or courier.

These objects are accomplished by explantation of plucked hair follicles on microporous membranes carrying human fibroblast feeder cells at their undersurface. In such primary cultures large numbers of ORS cells can be easily and repeatedly obtained irrespective of the donor's age. Such ORS cells may be used for the preparation of dermal or epidermal equivalents or kept frozen and stored in order to use them at a later time point. ORS cells used for the preparation of dermal or epidermal equivalents, when seeded once more on microporous membranes carrying fibroblast feeder cells, preferably human fibroblast feeder cells, at their undersurface, undergo tissue differentiation similar to that of normal epidermis, most probably due to a large compartment of proliferating cells. These improved culture conditions are important for the successful treatment of chronic wounds with epidermal equivalents generated in vitro from autologous ORS cells.

Clinical advantages of this technique as compared to grafting techniques of chronic wounds reported so far include noninvasiveness, so that the cells are available repeatedly, the lack of need for surgical facilities or anesthesia during the grafting procedure, and a short immobilization period of only 2 h required after grafting.

DETAILED DESCRIPTION OF THE INVENTION

Unless defined otherwise, all technical and scientific terms used herein have the same meanings commonly understood by one of ordinary skill in the art to which this invention belongs. Although any methods and materials similar or equivalent to those described herein can be used in the practice of the present invention, the preferred methods and materials are now described. All publications mentioned herein are incorporated in their entirety by reference.

The term "keratinocyte layer" as used herein means an in vitro generated keratinocyte tissue culture with more or less differentiated structure. The term epidermal equivalent as used herein means an in vitro generated organotypic tissue culture resembling in its histological structure the natural epidermis, especially concerning the stratification and development of the horny layer. A normal stratified epidermis consists of a basal layer of small cuboidal cells, several spinous layers of progressively flattened cells, a prominent granular layer and an orthokeratotic horny layer. All these layers can be detected in the epidermal equivalents that are subject of the invention. Localization of those epidermal differentiation products that have been assayed by immunohistochemistry (e.g., keratin, involucrin, filaggrin, integrins) is identical to that found in normal epidermis.

The term "autologous" as used herein means (1) that biological material is derived from the individual to be treated with epidermal equivalents, or (2) that biological material added to tissue cultures comes from the donor of the cells for tissue culture.

The term "homologous" as used herein means (1) that biological material is derived from one or more individuals of the same species as the individual to be treated with epidermal equivalents, or (2) that biological material added to tissue cultures comes from one or more individuals of the same species as the donor of cells for the tissue culture.

"Organotypic culture" and the like, refers to culture of cells under conditions that promote differentiation of the cells. Under conditions of organotypic culture, proliferation of the cells is slowed compared to culture under "proliferative" conditions such as primary culture conditions, and may be completely stopped. In the present case, an important condition for organotypic culture is maintenance of the cells at the air-liquid interface, a so-called "lifted" culturing condition.

Releasate from blood components, e.g., blood platelets, as used herein means any combination of cytokines or other growth factors obtained from blood components, e.g., blood platelets. Platelets stimulated with e.g., thrombin release the content of their alpha granules into the surrounding medium. Alpha granules usually contain several cytokines, e.g., platelet derived growth factor (PDGF), epidermal growth factor (EGF), transforming growth factors alpha and beta (TGF alpha/beta), platelet factor 4 (PF-4), platelet basic protein (PBP). However, it is possible to obtain cytokines and other growth factors from platelets by other methods than stimulating with thrombin. Moreover, other blood components produce growth factors and cytokines as well. Monocytes, e.g., produce IL-1, TNF alpha, IL-6 and other substances of interest; lymphocytes produce, e.g., keratinocyte growth factor (KGF).

General Method for Preparing Epidermal Equivalents From ORS Cells

ORS cells are obtained from the roots of hairs plucked from individuals to be treated with epidermal equivalents. Usually about 40 hair follicles are plucked from the scalp, and those in the anagen phase are then selected under the dissecting microscope. Usually it takes four weeks to obtain about 1 $cm^2$ of epidermal equivalents from five follicles. With improved culture and fermenter techniques it may be possible to get a higher yield, i.e., a larger area of epidermal equivalents, within this time.

The follicles are cleaned of microorganisms by incubation in an appropriate rinsing buffer, which contains antibiotics, e.g., fungizone and penicillin as well as streptomycin. Following this procedure hair bulbs and the infundibular parts are removed. The follicles are explanted and allowed to grow for several, usually 7–14, days, preferably 8 to 10 days. An optional step is passaging the primary culture and performing a secondary culture in order to obtain more cell material for the preparation of larger areas of epidermal equivalents. After expansion of the ORS cells to appropriate density ($10^3$ to $10^6$ cells per $cm^2$, preferably $5\times10^4$ to $1\times10^5$ cells per $cm^2$) they are dissociated and used for preparation of epidermal equivalents. Preferably, the cells are grown to confluence. Dissociation usually is performed with trypsin. Conditions used for dissociation are typical and general for keratinocyte culturing.

Epidermal equivalents are prepared by seeding ORS cells at appropriate density ($10^3$ to $10^6$ cells per $cm^2$, preferably $5\times10^4$ to $1\times10^6$ cells per $cm^2$, still more preferably $2-5\times10^5$ cells per $cm^2$, most preferably about $4\times10^5$ cells per $cm^2$) in culture devices suitable to grow them lifted to the air-liquid interface. One-half to three days after seeding, usually 1 day after seeding, the exposure of the ORS cells to air is performed, e.g., by aspiration of the medium inside the insert. The cultures are then continued about 10–20 days, preferably 14–18 days in such a "lifted" condition. The medium is changed periodically during the lifted cultured; preferably every two to four days, most preferably every three days.

The present invention also encompasses dermal equivalents, which include additional layers and so are more complex structures than epidermal equivalents. Dermal equivalents comprise differentiated ORS cells as their epidermal part and also a layer comprising a matrix component, preferably one containing embedded dermal fibroblasts and/ or other cells (a so-called "embedding matrix"). Dermal equivalents are made by placing a matrix, preferably a gel of collagen type I (e.g., as obtained from rat tail tendon) on the upper surface of the microporous membrane described above. When embedding human dermal fibroblasts, preferably autologous human dermal fibroblasts, the cells are embedded at a density of $10^3$ to $10^7$ cells per cm$^3$, preferably $10^4$ to $10^5$ cells per cm$^3$, most preferably about $5 \times 10^4$ cells per cm$^2$. The primary culture of ORS cells is then seeded on top of the matrix (preferably containing embedded dermal fibroblasts and/or other cells) and organotypic culturing is performed as described above. A detailed description of the preparation of dermal equivalents is provided by Limat et al. (Limat et al., Exp Cell Res 194:218–277 1991).

For preparing dermal equivalents, the embedding matrix can be made from biodegradable matrices, e.g., from different collagens or other matrix proteins or proteoglycans or materials such as polyhyaluronic acid, chondroitin sulfate. Mixtures of these materials can also be employed. Also synthetic biocompatible or biodegradable materials, such as silicones, can be used for the embedding matrix.

The cells embedded need not be limited to dermal fibroblasts; epidermal, mesenchymal, neuronal and/or epithelial cells can be included. The embedded cells are preferably obtained from skin tissue and are preferably homologous cells, most preferably autologous cells.

All culture steps are performed in an appropriate medium which allows the proliferation of the ORS cells and their outgrowth from the hair follicles. The medium is typically changed every 2–5 days, preferably every 3 days. Usually the medium for all steps is the same. The medium is typically based on a minimal medium and contains several additional ingredients. One common ingredient is serum, preferably of autologous or homologous origin, in a concentration of 0.5–60%, preferably 5–20%, most preferably about 10%. With the development of serum-free media, however, it may be possible to omit serum. Epidermal growth factor (EGF) stimulates migration of keratinocytes and delays their senescence which results in stimulation of proliferation. Cholera toxin, hydrocortisone, insulin, adenine and triiodothyronine have an effect of stimulating proliferation. All of these ingredients are thus useful in a medium for preparing epidermal equivalents. Nevertheless, it may be possible to omit or replace one or another of these ingredients.

Releasate from blood components, e.g., blood platelets, monocytes or lymphocytes, may serve as a source of cell proliferating activities and therefore may substitute serum and provide other above-mentioned ingredients. For certain culture periods the serum-containing medium might possibly be replaced by a defined, serum-free medium, e.g., SFM (Gibco Europe, Ettlingen).

Especially releasate from blood components, e.g., blood platelets, monocytes or lymphocytes, especially of homologous or autologous origin, may serve as a source of cell proliferating activities and therefore may substitute serum and provide other above-mentioned ingredients or indeed may provide additional ingredients. The blood components should be added to the culture medium in a concentration of 0.1% to 20%, preferably 1% to 5%, after the releasate is brought to the same final volume as the blood the components are obtained from. These releasates contain several growth factors that are present in serum, like PDGF, EGF or TGFs. However, serum as well as releasates contain many substances, and not all are characterized.

Releasate from blood platelets is obtained by centrifugation of anticoagulated whole blood, preferably human blood, in order to pellet all cells except thrombocytes. The supernatant is centrifuged once more to spin down the thrombocytes. The thrombocytes are suspended in an appropriate buffer, e.g., phosphate buffer and treated with thrombin in order to release their alpha granules which contain a mixture of growth factors, e.g., PDGF, PF-4, TGF-$\beta$, EGF, $\beta$-thromboglobulin. In a further centrifugation step all cellular material is removed. Finally, the supernatant is supplemented with buffer to the volume of the original blood sample from which the components are obtained. The blood components should be added to the culture medium in a concentration of 0.1% to 20%, preferably 1% to 10%, more preferably 2 to 5%.

Similarly, releasates can be obtained from other blood cells, such as monocytes, by breaking up the cells, e.g., by sonication or a freeze thaw method, and purifying the growth factors, e.g., by filtration or immunological methods.

The blood component releasates can also be used to condition the wound bed in the course of grafting the epidermal or dermal equivalents. Furthermore, the culture medium containing the releasates and used to perform the organotypic culturing step, after having been conditioned by the cells, can be used to condition the bed of the skin defect in the course of grafting the epidermal or dermal equivalents.

Cultivation usually is performed in inserts with microporous membranes, which contain homologous or autologous dermal fibroblasts (HDF), especially postmitotic HDF at their undersurface. HDF secrete factors that condition the medium in order to get a better growth of the epidermal equivalents. The HDF layer can be formed from between $5 \times 10^3$ to $1 \times 10^5$ cells, preferably about $1 \times 10^4$ to $5 \times 10^4$ cells. The HDF are preferably postmitotic, but earlier passage cells can be used if they are irradiated, treated with mitomycin C or otherwise treated to inhibit their proliferation but maintain their metabolism.

Microporous membranes are suitable as a culture substrate, because they allow substances to diffuse from one side to the other, but work as a barrier for cells. The pore size of the membrane is not a limitation on the invention, but should be adequate to allow diffusion of proteins of up to 100,000 Da molecular weight, preferably of up to 70,000 Da molecular weight. The membrane should at least allow diffusion of small hormones such as insulin, and allow passage of proteins of up to 15,000 Da molecular weight. Other means than a microporous membrane for performing the function of allowing diffusion of soluble factors to the cultured ORS cells, while preventing mixing of the ORS cells with the HDF would also be usable.

The microporous membranes typical in the art are usually used. However, membranes fabricated from a biodegradable material, e.g., polyhyaluronic acid or polylactic acid can also be used. When a biodegradable microporous membrane is employed it is contemplated that the entire culture, including the differentiated ORS cells, the microporous membrane and the HDF, will be transplanted into the skin defect. Thus, in this alternative embodiment, the HDF grown on the underside of the membrane need not be post-mitotic or treated to preclude proliferation. While HDF tend to be less immunogenic than keratinocytes, it is preferable that when this embodiment is employed, the HDF be homologous cells, preferably autologous cells.

For practical reasons our experiments were performed with epidermal equivalents of 6 or 8 mm diameter. Further clinical treatments will allow to determine, if this size is generally applicable or if other sizes will be more convenient in at least some cases.

In many cases the epidermal equivalents will have to be delivered from the facility where they are generated to the institution where they are used. Therefore a system is needed to enable the transport of the epidermal equivalents. Generally it will be convenient to put the epidermal equivalents onto a carrier and preferably adhere them to the carrier. As an adhesive, fibrin glue is preferred. Other options may be extracellular matrix components such as collagen, fibronectin, proteoglycans (hyaluronic acid, chondroitin sulfate etc.), or basement membrane zone components such as laminin, Matrigel™, or L-polylysine, or further tissue glues. The epidermal equivalents may also be adhered to the carrier in a physical manner by using substances like silicone, vaseline or similar semi-solid substances. The epidermal equivalents are preferably adhered to the carrier with their horny layer in contact with the carrier. The carrier might consist of a synthetic membrane, made from at least one of, e.g., polyester, PTFE or polyurethane, or one made from a biodegradable polymer, e.g., at least one of hyaluronic acid, polylactic acid or collagen; it might be as well a silicone or vaseline gauze dressing or any other material suitable for wound dressing in order not to have to remove the carrier immediately after the dermal or epidermal equivalents are transplanted, but rather to allow the carrier to remain in place to immobilize the implanted dermal or epidermal equivalents for several days.

The dermal or epidermal equivalents put onto the carrier have to be kept in a condition ready for grafting. Irrespective of whether the microporous membrane is removed from the basal cell layer for transport, conditions resembling those during cultivation seem to be favorable. In order to keep the dermal or epidermal equivalents in contact with medium only from the basal layer, like during cultivation, agarose in a concentration from 1% to 5%, preferably in a concentration of 1 to 3%, or methyl cellulose or any other gelifying substance in comparable concentrations, may be used to solidify the medium. The epidermal equivalents together with the carrier will be placed with their basal layer on top of the solidified or gelled medium. The whole device is closed air tight, and shipped. The epidermal equivalents are most preferably used for grafting within 24 hours of packaging.

The dermal or epidermal equivalents are transplanted by simply placing them in the bed of the wound or other skin defect. Preferably the dermal or epidermal equivalents are immobilized, preferably for at least 2 hours, more preferably by use of a biodegradable material, by some sort of tissue glue or a bandage such as described above for the transport carrier material. As described above, the bed of the skin defect can be treated with blood releasates or the medium from the organotypic culturing prior to or coincident with the transplantation.

EXAMPLE 1

Preparation of the ORS Cells

About 40 hair follicles were plucked with tweezers from the occipital scalp of individuals, and those in the anagen phase, as detected by well-developed root sheaths, among other characteristics, were then selected under the dissecting microscope (Limat and Noser, J Invest Dermatol 87: 485–488, 1986; Limat et al., J Invest Dermatol 92: 758–762, 1989). The hair bulbs as well as the infundibular parts were removed with microsurgical blades.

HDF were derived from skin explants of a healthy, repeatedly HIV- and hepatitis-serology negative individual and cultured in DMEM supplemented with 10% FCS or human serum.

Usually, six follicles were explanted on the microporous membrane of a cell culture insert (Falcon 3090; Becton Dickinson, Franklin Lanes, N.J.) that carried on its undersurface a preformed feeder layer made of $10^5$ postmitotic human dermal fibroblasts (HDF) (Limat et al., J Invest Dermatol 92:758–762, 1989).

For the purpose of getting a efficient outgrowth of the ORS cells from the hair follicles and a high proliferation rate, it is important not to place the HDF feeder cells at the bottom of the culture dish, resulting in an additional medium layer between the HDF layer and the microporous membrane supporting the ORS cells. Growing each cell type at one side of the microporous membrane allows a very close interaction, but prevents cross contamination of the ORS cells with fibroblasts and thus guarantees a pure culture of ORS cells.

The culture medium consisted of Dulbecco's modified Eagle's medium/F12 (3:1) supplemented with 10% human serum, 10 ng of epidermal growth factor per ml, 0.4 microgram of hydrocortisone per ml, 0.1 nM choleratoxin, 0.135 mM adenine, and 2 nM triiodothyronine (all from Sigma Chemical Co., St. Louis, Mo.), final $Ca^{2+}$ concentration 1.5 nM (Wu et al., Cell 31: 693–703, 1982; Limat and Noser, J Invest Dermatol 87: 485–488, 1986). Earlier experiments had been performed with 10% fetal calf serum (FCS, Boehringer Mannheim, Germany). However, using human serum in order to reduce the number of allogeneic ingredients, with the present culture technique the outgrowth and proliferation of the ORS cells was superior. Within about 2 weeks, the ORS cells expanded and reached confluence. They were dissociated with trypsin/EDTA 0.1%/0.02%, checked for viability, and used for preparation of epidermal equivalents. To further avoid not fully defined ingredients human serum was omitted and replaced by, e.g., lipid molecules such as retinol and/or retinol derivatives and growth factors such as PDGF, FGF, EGF which act as survival factors for the feeder fibroblasts and initiators of the cell cycle, respectively, in the absence of serum.

Explanting plucked anagen hair follicles directly on the membrane of culture inserts carrying postmitotic HDF on the undersurface as feeder cells proved to be a simple, efficient, and reproducible method for establishing primary cultures of ORS cells. About 80% of the explanted hair follicles gave rise to outgrowth of ORS cells, even when derived from individuals aged up to 91 years. After 14 days, large areas of the insert were covered by compactly arranged small cells, at which time they were used for preparation of epidermal equivalents.

Comparison of the growth behavior of 70 strains of ORS cells derived from 30 donors revealed no significant differences between young (21 donors aged 19–50 years) and old (9 donors aged 51–93 years) donors. About $0.5 \times 10^6$ cells were usually obtained per explanted follicle. Cell viability was usually higher than 95%. In the absence of postmitotic HDF as a feeder layer, there was only sporadic outgrowth of ORS cells.

EXAMPLE 2

Preparation of Epidermal Equivalents

ORS cells harvested from primary cultures were seeded at a density of $1 \times 10^5 - 5 \times 10^5/cm^2$ on cell culture inserts (Falcon 3095) carrying $5 \times 10^4$ postmitotic HDF on the undersurface of their microporous membrane. As was the case in the culture of the ORS cells, it is important to keep the HDF feeder cells in close contact with the ORS cells while separating them by the microporous membrane. This enhances proliferation as well as differentiation and thus the homeostasis of the developing tissue. Culture medium was the same as for the preparation of primary cultures (see above), again with the option to replace human serum by, e.g., retinol and/or retinol derivatives as survival factors for the feeder fibroblasts and initiators of the cell cycle, respectively, in the absence of serum (Y. Chen et al., Proc Natl Acad Sci USA 94:10205–10208 (1997). After 24 h, the ORS cells were exposed to air by aspiration of the medium inside the insert (leaving the underside of the insert in contact with medium) and then cultured for 12–14 days with 3 medium changes per week.

For transplantation, the epidermal equivalents were excised from the insert together with the underlying membrane by means of a 6 mm punch (Stiefel Laboratorium) and positioned upside down on a punched out polyester membrane (Thomapor 95877, Reichelt Chemie, Heidelberg, Germany) of 6 mm diameter. In one patient additional epidermal equivalents of 8 mm diameter were prepared likewise. The insert membrane together with the attached postmitotic HDF was then carefully removed by means of fine tweezers.

The epidermal equivalents on their supporting polyester membrane were washed in Dulbecco's phosphate-buffered saline (PBS) and left floating therein until their application on the wound bed, usually for no longer than 30 min.

ORS cells harvested from primary cultures and cultured at the air-liquid interface on insert membranes carrying postmitotic HDF at their undersurface developed a stratified epithelium within 14 days. This consisted of a basal layer of small cuboidal cells below a thick suprabasal compartment of progressively flattened cells. A prominent granular layer as well as an orthokeratotic horny layer were present.

Based on 80% of follicles giving rise to ORS cell outgrowth, about 5 anagen hair follicles were needed to generate 1 cm$^2$ of epidermal equivalents. The period to generate graftable epidermal equivalents usually was 4 weeks, i.e., two weeks for the primary culture and two weeks for the organotypic culture.

EXAMPLE 3

Treatment of Chronic Wounds with Epidermal Equivalents

Five people (one male, four females, aged 58 to 91) suffering from recalcitrant chronic leg ulcers (four of them with more than two ulcers on the same leg, duration at least four years; venous or mixed arterial and venous disease in four, in one additional diabetes mellitus, primary lymphoedema in one) were treated with epidermal equivalents obtained from autologous ORS cells. The ulcers were cleaned conventionally (primarily with hydrocolloidal dressings and topical antimicrobial agents) until ready for grafting. Then up to 20 autologous epidermal equivalents, usually 6 mm, in one ulcer 8 mm in width, were placed basal layer downward on the surface of the ulcers, and the supporting polyester membranes were carefully removed with fine tweezers. This grafting procedure was performed at the bedside; no anesthesia was needed. In four of the patients, further ulcers on the same leg served as controls. All ulcers were then covered with a transparent, semiocclusive dressing (Tegaderm; 3M, London, Canada) overlaid by an elastic bandage with compression adapted to the patient's arterial status. The patients were immobilized for 2 h immediately after grafting. After 3 days, the semiocclusive dressing was carefully removed and a hydropolymer dressing (Tielle; Johnson & Johnson Medical, Ascot, UK) applied, again overlaid by the elastic bandage. The hydropolymer dressings were then changed every 2 to 5 days. After complete re-epithelialization local treatment was switched to topical emollients. Take of the grafts and healing of the ulcers was documented by standardized photographs taken on each change of dressings.

A total of 11 ulcers were treated, seven of them by covering about 90% of the ulcer surface with densely arranged cultures, four by putting isolated cultures into the central parts. On the first change of the dressing 3 days after grafting, about 80% of the grafts were visible and adherent to the wound bed in both types of treatment. Within the following 2 to 3 weeks the grafts consolidated in five of the seven densely grafted ulcers, resulting in complete re-epithelialization and healing. In the two remaining, chronically-infected (Pseudomonas) ulcers, the grafts were partly destroyed, which led to delayed healing by 4 to 5 weeks. In the ulcers treated by isolated grafts, there was accelerated formation of granulation tissue and re-epithelialization mainly from the wound edges, as compared to the ulcers on the same leg treated with the dressings only. In this type of treatment, permanent take with subsequent expansion of the grafts resulting in complete re-epithelialization was only documented for the one ulcer treated with larger epithelial sheets measuring 8 mm in diameter. The control ulcers in the four patients with more than two ulcers on the same leg were only slightly improved after 3 weeks, at which time they were treated either by further grafting of autologous epidermal equivalents or by conventional surgery.

After re-epithelialization, the epidermis was initially still fragile with some tendency to blistering after minor frictional trauma, occasionally resulting in small erosions. These erosions re-epithelialized rapidly under conventional topical treatment. The first patients have now been followed up for more than one year and show increasing stabilization of the treated areas and no recurrence of the ulcers so far.

EXAMPLE 4

Mixed Autologous and Allogeneic Epidermal Equivalents

For producing epidermal equivalents for larger wounds, it is possible as an alternative embodiment to combine autologous ORS cells with allogeneic keratinocytes in the following fashion.

According to the step described in Example 2, first ORS cells may be seeded in a density of $1 \times 10^4$ to $1 \times 10^5$ as a thin layer onto the microporous membrane and then, after attachment of these to the membrane, after about 8 to 24 h, allogeneic keratinocytes are seeded in a density of $3 \times 10^4$ to $5 \times 10^5$ on top of them. The result is an epidermal equivalent consisting of an autologous basal layer and allogeneic layers on top of them.

EXAMPLE 5

Transport System

A petri dish with 10 cm diameter is filled with 25 ml of the same medium as used for generating the epidermal equivalents plus 3% agarose or other hydrocolloidal materials such as alginates, gelatin, pectins, polyurethane, polyvinyl alcohols, silicone, etc. Epidermal equivalents are excised from the insert together with the underlying membrane and may be positioned upside down on a biodegradable polyhyaluronic acid membrane (Fidia Biopolymers, Italia), favourably fixed with a fibrin glue in a fashion representing the shape of the wound to be treated. The epidermal equivalents fixed on the membrane are then placed with their basal layer onto the agarose containing medium in the petri dish. The petri dish is closed with parafilm. The whole package is shipped overnight to the physician performing the grafting procedure.

After unpackaging, the polyhyaluronic acid membrane together with the epidermal equivalents is lifted from the agarose containing medium. The insert membranes together with the attached postmitotic HDF are carefully removed by means of fine tweezers. The epidermal equivalents are grafted onto the wound together with the polyhyaluronic acid membrane. The wound is then covered, for example, with a transparent, semiocclusive dressing overlaid by an elastic bandage in a manner similar to the above mentioned examples.

what is claimed is:

1. A method for treating a skin defect comprising applying to said skin defect a portion of epidermal tissue comprising cultured outer root sheath cells.

2. The method of claim 1, wherein said outer root sheath cells are autologous cells.

3. The method of claim 1, wherein said epidermal tissue comprises outer root sheath cells cultured in a medium having only homologous or autologous biological supplements.

4. The method of claim 1, further comprising treating the bed of said skin defect with releasates from homologous or autologous blood components.

5. A composition for treatment of a skin defect comprising differentiated outer root sheath cells formed into a dermal or an epidermal equivalent and a carrier suitable for immobilizing said dermal or epidermal equivalent within said skin defect.

6. The composition of claim 5, wherein said carrier is a synthetic membrane.

7. The composition of claim 6, wherein said membrane is a polyester, PTFE, polyurethane membrane.

8. The composition of claim 5, wherein said carrier is a biodegradable membrane.

9. The composition of claim 8, wherein said biodegradable membrane comprises at least one of polyhyaluronic acid, polylactic acid or collagen.

10. A process for making a composition for healing a skit defect, comprising:

a) primary culturing outer root sheath cells by explanting hair follicles and culturing them submerged in medium on a microporous membrane, on the undersurface of which a feeder layer of human dermal fibroblasts is placed;

b) organotypically culturing said outer root sheath cells on a microporous membrane, on the undersurface of which a feeder layer of human dermal fibroblasts is placed, at the air-liquid interface of the medium.

11. The method of claim 10, wherein the culture medium comprises releasates from blood components.

12. The method of claim 11, wherein said releasates are obtained from at least one cell type selected from the group consisting of platelets, monocytes and lymphocytes.

13. The method of claim 12, wherein said at least one cell type is of homologous or autologous origin.

14. The method of claim 10, further comprising the step of c) adhering said organotypically cultured outer root sheath cells to a carrier suitable for contacting said epidermal equivalent with a skin defect and immobilizing said epidermal equivalent at the site of contact.

15. A system for transporting epidermal equivalents or other skin tissue, comprising a container filled with a gelled or solid culture medium, and a carrier, wherein said epidermal equivalents or other skin tissue are fixed to said carrier and contacted with said culture medium such that said epidermal equivalents or other skin tissue are interposed between said culture medium and said carrier.

16. The system of claim 15, wherein said carrier is a membrane comprising at least one material selected from the group consisting of polyester, PTFE, polyurethane, polyhyaluronic acid, polylactic acid and collagen.

17. A composition for treatment of skin defects comprising a differentiated outer root sheath cells contacting a biocompatible or biodegradable matrix.

18. The composition of claim 17, wherein said matrix comprises at least one material selected from the group consisting of silicone, collagen, at least one proteoglycan, at least one extracellular matrix protein, polyhyaluronic acid and chondroitin sulfate.

19. The composition of claim 17, wherein said matrix has embedded in it cells of at least one type selected from the group consisting of human dermal fibroblasts, epidermal cells, mesenchymal cells, neuronal cells and endothelial cells.

* * * * *